(12) United States Patent
Frankenberger et al.

(10) Patent No.: US 7,476,380 B2
(45) Date of Patent: Jan. 13, 2009

(54) METHODS FOR TREATING ILLNESSES OF THE TRACHEO-BRONCHIAL TRACT, ESPECIALLY CHRONIC OBSTRUCTIVE PULMONARY DISEASE (COPD)

(75) Inventors: Marion Frankenberger, Munich (DE); Konrad Maier, Munich (DE); Gerhard Scheuch, Gemunden (DE); Hans-Werner Ziegler-Heitbrock, Herrsching (DE)

(73) Assignee: GSE-Forschungszentrum fur Umwelt und Gesundheit GmbH, Neuherberg (DE)

( * ) Notice: Subject to any disclaimer, the term of this patent is extended or adjusted under 35 U.S.C. 154(b) by 0 days.

(21) Appl. No.: 11/127,986

(22) Filed: May 12, 2005

(65) Prior Publication Data

US 2005/0220859 A1 Oct. 6, 2005

Related U.S. Application Data

(60) Division of application No. 10/241,181, filed on Sep. 11, 2002, now Pat. No. 7,074,389, which is a continuation of application No. PCT/EP01/02832, filed on Mar. 13, 2001.

(30) Foreign Application Priority Data

Mar. 13, 2000 (DE) .............................. 100 12 151

(51) Int. Cl.
  *A61K 9/12* (2006.01)
  *A61K 9/14* (2006.01)
  *A61K 9/127* (2006.01)
  *A61K 9/133* (2006.01)

(52) U.S. Cl. .................... 424/45; 424/46; 424/450; 424/489; 514/724; 514/725; 514/559; 514/826

(58) Field of Classification Search ................. 424/45, 424/46, 450, 489; 514/724, 725, 559, 826
See application file for complete search history.

(56) References Cited

U.S. PATENT DOCUMENTS

| | | | | |
|---|---|---|---|---|
| 4,839,175 A | * | 6/1989 | Guo et al. | .................... 424/450 |
| 5,006,343 A | * | 4/1991 | Benson et al. | .............. 424/450 |
| 5,306,483 A | * | 4/1994 | Mautone | ....................... 424/45 |
| 5,556,611 A | * | 9/1996 | Biesalski | ..................... 424/46 |
| 6,183,774 B1 | * | 2/2001 | Aust et al. | ................... 424/450 |

* cited by examiner

*Primary Examiner*—Mina Haghighatian
(74) *Attorney, Agent, or Firm*—Jenkin, Wilson, Taylor & Hunt, P.A.

(57) ABSTRACT

The invention describes a means for the treatment of diseases of the tracheo-bronchial tract, particularly of COPD.

8 Claims, 7 Drawing Sheets

METHODS FOR TREATING ILLNESSES OF THE TRACHEO-BRONCHIAL TRACT, ESPECIALLY CHRONIC OBSTRUCTIVE PULMONARY DISEASE (COPD)

RELATED APPLICATIONS

This application is a division of U.S. patent application Ser. No. 10/241,181, filed Sep. 11, 2002, now U.S. Pat. No. 7,074,389 which itself is a continuation of PCT patent application number PCT/EP01/02832, filed Mar. 13, 2001, which claims priority to German patent application number 10012151.9, filed Mar. 13, 2000, the disclosures of each of which are incorporated herein by reference in their entirety.

DESCRIPTION

The invention relates to a means for the prophylaxis and therapy of disorders of the tracheo-bronchial tract, particularly of COPD (chronic obstructive pulmonary disease).

TECHNICAL FIELD

Typically, COPD is encountered in smokers. The disease is characterized by chronic inflammation of the small airways (<2 mm) which unavoidably results in tissue reconstruction and irreparable narrowing (obstruction) of this portion of the airways.

BACKGROUND ART

Detailed tissue examination of these small airways shows increased production of mucus, increase in muciferous goblet cells, smooth muscle hypertrophy as well as infiltration with pigment-charged macrophages and CD8 positive T lymphocytes. As this process continues, tissue reconstruction and an increased deposition of connective tissue fibers occur.

Pathophysiologically, it is the inflammation which is most important. It is characterized by an infiltration of the small airways tissue with neutrophile granulocytes, macrophages, and lymphocytes. This infiltration into the tissue is facilitated by the production of proteases by leucocytes. Mediators are produced within the tissue which promote mucus formation, stimulate muscle cells and support the generation of connective tissue (collagen) fibers by fibroblasts.

In examinations of the respiratory mechanic, COPD shows a decreased maximal expiratory flow ($FEV_1$) and a slow forced emptying of the lungs. COPD is often associated with chronic bronchitis and emphysema. However, these two diseases can be clearly distinguished from COPD.

Clinically, chronic bronchitis is defined by a chronic productive cough for at least 3 months per year in at least 2 successive years. This disease is characterized by common bacterial infections and it can but does not necessarily lead to an irreversible obstruction.

Emphysema is defined as an irreversible dilatation of the airways distal of the terminal bronchia caused by degradation of the alveolar septs associated with a degradation of elastic fibers. Emphysema is not accompanied by fibrosis.

Thus, COPD may be differentiated as an entity from chronic bronchitis and emphysema although COPD may be accompanied by these two diseases.

Predominantly, COPD affects the small airways while chronic bronchitis occurs in the large and medium airways and emphysema in the alveoles.

COPD is an irreversible process resulting in tissue rearrangements accompanied by a fibrosis (an increase in fibers). Chronic bronchitis does not result in tissue rearrangements. In emphysema, destruction of the alveolar septs, is observed.

An increase in neutrophile granulocytes, macrophages, and CD8 cells in the small airways has been found to be typical in COPD. All inflammatory cells are involved in chronic bronchitis while leucocytes are of no major importance in emphysema.

It is known from EP 0 352 412 to use esters of retinoic acid and/or an ester of retinol in the preparation form of an aerosol inhalant for topical application by inhalation to prevent and treat mucous membrane disorders of the tracheo-bronchial tract in humans and animals. These so-called bronchitides include acute and chronic bronchitides which show no obstruction. For example, the majority of smokers suffers from chronic bronchitis without showing airway obstruction and thus COPD. Bronchiectases are irreversible, cylindric, saccular or varicoid dilatations of the bronchia, a syndrome not belonging to the chronic obstructive disease, COPD.

Therefore, the mucous membrane disorders of the tracheo-bronchial tract mentioned in EP 0 352 412 do not belong to the diseases to be subsumed under the term COPD. They differ from COPD particularly in that they do not show the irreversible obstruction typical for COPD.

Up to now, COPD has been treated for example by administration of β-adrenergics/anticholinergics, theophyllin, and/or glucocorticoids. Disadvantages of the above-mentioned medicaments are that their activity is only symptomatic and that they have no effect on the fatal course of COPD. Spasmolytics have a life shortening effect. Theophyllin causes arrhytmias. An important side effect of glucocorticoids is osteoporosis.

SUMMARY

It is an object of the present invention to provide a novel means for the treatment of COPD which avoids the disadvantages known from the prior art.

According to the invention, this object has been achieved by using vitamin A and/or the derivatives and/or the esters thereof in a therapeutically effective amount in the therapy of COPD applied in the form of an aerosol inhalant.

The term "derivatives" of vitamin A comprises retinol, retinal, and retinoic acid and the derivatives and esters of each of these compounds as well as β-carotene and its derivatives being the precursor of vitamin A. For example, retinol may be esterified with saturated and unsaturated fatty acids such as linoleic acid, stearic acid, palmitic acid, oleic acid. This includes also chemical modifications of the fatty acids and alcohols mentioned. (See also EP 0 352 412 B1; page 11, claim 4+claim 6). Martindale, The Extra Pharmacopeia, 1982, London, The Pharmacuetical Press, and all subsequent editions is mentioned as an example. This document is incorporated herein by reference in its entirety.

For administration by inhalation, vitamin A is applied in the form of an aerosol wherein particularly sprays and inhalants are used. This achieves the dispersion of the active agent into very small particles to transport it to the site of its therapeutic effectiveness.

According to the invention, vitamin A and the derivatives and esters thereof are present in the form of an aerosol. Aerosols are fine mists usually obtained by systems under pressure. They may be obtained for example by spraying or atomizing liquids but also of dry powders. Aerosols for inhalation are different from those systems usually referred to as aerosols in that the aerosol particles are present in a size lower than 10 μm, preferably in the range of 1-10 μm.

The essential components of aerosol systems in the form of sprays are for example a container containing a propellant while today also aerosol systems without propellant have been developed. Furthermore, the aerosol system contains the active ingredient(s) together with conventional auxiliary agents such as for example propellants and lactose. The composition of these components determines the properties of the aerosol inhalant, i.e. for example the particle size distribution, delivery rate, viscosity, etc.

Aerosols may be obtained as two-phase aerosols (gas and liquid) or three-phase aerosols (gas, liquid, and solid or liquid). Two-phase aerosols consist of a solution of the active agent in a liquefied propellant and of the atomized propellant. The solvent for example comprises the propellant or a mixture of the propellant and co-solvents such as alcohol, propylene glycol, and polyethylene glycols often used to ameliorate the solubility of the active agents.

Three-phase systems comprise a suspension or emulsion of the active ingredient or ingredients, respectively, together with the atomized propellants. A suspension includes the active agent dispersed in the propellant system using conventional auxiliary agents such as wetting agents and/or solid carriers such as talc or colloidal silica. Propellants are known and comprise several carbohydrates, if possible those without damaging impact on the ozone layer.

An inhalation is only possible if the solutions for inhalation are atomized into very small particles of a size in the range of 1-10 μm. Only those finely dispersed aerosols can be inhaled at all. An inhalation is contra-indicated in the case of conventional aerosols. For further information with respect to aerosol inhalants see for example the US Pharmacopoeia which is incorporated herein by reference in its entirety.

In a preferred embodiment of the invention, vitamin A is encapsulated in liposomes. Liposomes are aqueous compartments surrounded by a completely closed lipid bilayer. Liposomes are for example generated artificially by suspending suitable lipids in aqueous solutions. The liposomes are dispersed to generate closed vesicles of an approximately equal size. Into the aqueous solutions and the lipid membranes, respectively, may then be incorporated foreign molecules, vitamin A according to the present invention. It has been shown that vitamin A packaged into liposomes can enhance the therapeutic effect and efficiently reduce side effects. Further details in this respect are explained in the following.

It has been shown that liposomes containing at least phosphatidylcholine together with at least another phospholipid selected from phosphatidylinositol, phosphatidylserine, phosphatidic acid and cardiolipin are particularly suitable for the treatment of COPD. The use of these specifically composed liposomes results in selective uptake by alveolar macrophages, a higher specificity of the therapy and a reduction of the therapeutically effective dose in association with reduced side effects.

The amount of phosphatidylcholine is approx. 50-95% while the amount of the other phospholipids is 5-50%, each based on 100% phospholipids. Thus, phosphatidylcholine is an essential component of the liposomes while the remainder, i.e. the other 5-50%, may be one or more of the above-mentioned phospholipids. The liposomes of the present invention further contain antioxidants in an amount of 10-50%. Preferred in this respect is vitamin E or the derivatives thereof such as (+)-α-tocopherol acetate, (±)-α-tocopherol acetate, (+)-α-tocopherol acid succinate. The amount of phospholipids is 50%-90%.

The amount of vitamin A encapsulated into the liposomes may be determined by those skilled in the art by conventional medical-therapeutic testing using the pure substance. It should be understood that these tests have to be carried out in animals beforehand. It is sensible to use also the liposome formulation described as an aerosol content to achieve optimal therapeutic effects.

To date, vitamin A preparations have not been described as aerosol inhalants in the form of the specifically composed liposomes described herein. A pharmaceutical preparation of this type may not only be used in the treatment of COPD but e.g. also for the treatment of chronic bronchitides, emphysemas and malignant as well as benign lung diseases and generally in the treatment of disorders of the tracheo-bronchial tract.

The liposomes used according to the invention differ from the multilamellar liposomes known from the prior art not only in their composition but also in that they are obtained in an unilamellar state. The specific combination of liposome organization, active agent, and structure results in the surprising efficacy found according to the present invention in the treatment of diseases of the tracheo-bronchial tract.

Preferably, such phospholipids are employed which enable a selective targeting of alveolar macrophages by binding to specific receptors present on alveolar macrophages, the so-called scavenger receptors. This includes the following phospholipids:

1. phosphatidylinositol (1,2-diacyl-sn-glycero-3-phospho-[1-D-myo-inositol])

The acyl residues may be derived from arachidonic acid or from linoleic acid, palmitic acid, stearic acid and other unsaturated or saturated fatty acids 2. phosphatidylserine (1,2-diacyl-sn-glycero-3-phospho-serine)

The acyl residues may be derived from arachidonic acid or from oleic acid, palmitic acid and other unsaturated and saturated fatty acids 3. phosphatidic acid (1,2-diacyl-sn-glycero-3-phosphate)

The acyl residues may be derived from arachidonic acid or from stearic acid, decanoic acid, heptadecanoic acid, lauric acid, myristic acid, octanoic acid, oleic acid, palmitic acid, and other unsaturated or saturated fatty acids 4. cardiolipin (diphosphatidylglycerol])

Cardiolipin contains a maximum of 4 acyl residues derived from unsaturated and saturated fatty acids 5. phosphatidycholine (L-α-lecithine, 1,2-diacyl-sn-glycero-3-phosphocholine) (partially oxidized)

The acyl residues may be derived from arachidonic acid or from unsaturated or saturated fatty acids. At least 1 acylic ligand is unsaturated. The unsaturated acyl residue is partially oxidized and mediates the binding of the liposomes to scavenger receptors.

The liposomes employed according to the present invention preferably have a size in the range of 0.1 μm to 2 μm, particularly preferred of 0.4 μm. The use of unilamellar liposomes is particularly preferred. Their preparation is carried out by a type of high pressure filtration, for example using an extruder commercially available from Lipex Biomembranes company, Canada. Conventional liposomes such as those described for example in the article by Parthasarathy et al., Cancer Chemother. and Pharmacol. 1999, 43(4), 277-283, are prepared by reconstitution of a dry lipid film in the desired liquid. This results in so-called multilamellar liposomes, i.e. liposomes having several lipid layers surrounding the aqueous core. Such liposomes are quite heterogenous in size and may be brought to uniform size by means of sonication, as shown in Parthasarathy et al., after which, however, they still remain multilamellar. However, the multilamellar liposomes described in Parthasarathy et al. tend to form aggregates or fuse to form still larger liposomes. The use of such liposomes has been found unsuitable according to the invention. By using the extruder described above and has been mentioned exemplarily only the finished reconstituted liposomes may be washed prior to use so that substances which have not been incorporated are removed, on the other hand the unilamellar liposomes having only one lipid layer around the aqueous core are further processed which renders them particularly stable. It is the combination of the lipid composition described herein and the use of unilamellar liposomes which leads to a particularly significant therapeutic efficiency.

The object, namely to deliver the active agent to specific target cells, i.e. alveolar macrophages, can only be achieved by using the liposome preparation provided according to the invention. Only this specific composition of the liposomes ensures that these are recognized and actively taken up by specific target cells. In this manner it is possible to achieve an effect of vitamin A in alveolar macrophages as the relevant target cells which has neither been known nor described up to now.

The use of the pharmaceutical composition according to the invention results in a very specific modification of the metabolism of a certain type of leucocytes in the lung, namely the alveolar macrophages, to strongly affect the inflammatory process, particularly of COPD.

It has not been known from the prior art that cellular targeting can be achieved by using a particular liposomal composition to bring about novel therapeutic possibilities. Cellular targeting of the liposome composition selected according to the invention is the prerequisite for the solution of the problem underlying the present invention in other, i.e. not-alveolar macrophages, another effect of vitamin A may be considered which could even compromise the above-mentioned object. Such an effect has been described for example to occur in rat osteoblasts.

In Kirilenko V. N. and Gregoriadis G., J. Drug Targeting 1993, 1(4), 361-368 lipids are described as emulsifiers enhancing the unspecific resorption of vitamins during food intake. The particular composition used according to the invention is not described, and the use for a treatment of diseases of the tracheo-bronchial tract, particularly of COPD, is not suggested. Only the specific composition used herein provides the possibility to transport vitamin A to specific target cells by which it can be actively incorporated.

In EP-A-0 229 561 liposomes are used as carriers to transport vitamin A to skin cells. The composition used exclusively shows cosmetic but no therapeutic effects. It is unthinkable to use these compositions in the tracheo-bronchial tract. The liposomes mentioned in EP-A-0 229 561 also lack the property of recognizing a particular target cell in the lung to be incorporated by this cell in a highly specific manner.

In addition, also EP-A-0 352 412 is not prejudicial as to the novelty of and does not render obvious the object of the present invention. Although it describes the treatment of the bronchial epithelium by vitamin A it does not use the specific liposomal preparation according to the invention.

BRIEF DESCRIPTION OF THE DRAWINGS

In the following the invention will be described with respect to the accompanying Figures. The Figures show.

BAL=bronchio-alveolar lavage
TNF=tumor necrosis factor
AM=alveolar macrophages
ELISA=enzyme linked immunosorbent assay

DETAILED DESCRIPTION

In the following, the present invention will be described in more detail with respect to Examples to which the invention, however, is not limited.

There is increasing evidence that disorders in the protease/protease inhibitor equilibrium are the cause underlying the pathogenesis of chronic lung diseases. Thus, it has been demonstrated that matrix metalloproteases (MMPs) secreted by alveolar macrophages lead to irreversible damages of the lung tissue and thus result in a decrease of respiratory functions. This is particularly true for patients suffering from chronic obstructive bronchitis (COPD). Among the MMPs in COPD, it is particularly the secretion of MMP-9 metalloprotease which is increased in the airways and alveoles and can no longer be completely neutralized by its natural antagonist TIMP-1 (tissue inhibitor of metalloprotease). The alveolar macrophage has been suggested to be the main producer of MMP-9 in the lung and it (and not the neutrophile granulocyte as supposed up to now) has also been discussed as the main responsible for the formation of emphysemas in most recent studies in rat. Our own studies show that MMP-9 is also increased in the serum of COPD patients. An important criterion to determine the degree of the disturbance of the protease/antiprotease equilibrium is the proteinase-to-inhibitor ratio: MMP-9/TIMP-1.

Using an in vitro system with alveolar macrophages it has been shown according to the invention that vitamin A not only significantly inhibits MMP-9 expression but surprisingly at the same time also significantly stimulates the expression of the specific inhibitor TIMP-1. These effects were most pronounced if vitamin A was previously packaged into the specifically composed liposomes described above which ensures the specific uptake by alveolar macrophages.

Unexpectedly, by using liposome-encapsulated vitamin A the ratio of MMP-9/TIMP-1 could be clearly reduced, i.e. by a factor of 12. This means an efficient reduction of the tissue destructive potential of the proteolytic system by vitamin A. On the basis of these studies the present therapy approach for the treatment of COPD and lung emphysema has been established. The composition of the liposomes is already described above. The following Examples explain in detail the preparation of the liposomes.

The effect of vitamin A on metalloproteases is known. However, the results achieved by the administration of vitamin A are very contradictory. While in several test systems there has been reported a reduction in metalloprotease concentration by inhibition of the expression of the respective coding genes, others describe an increased expression and thereby an increased concentration of metalloproteases. Park and Kim, Mol. Cells 1999, 9(2):119-26 describe that due to the effect of retinoic acid enzymes having gelatinase activities which are to be counted among the metalloproteases were increased in their activity, particularly the expression of these metalloproteases was increased. The publication of Overall, Journal of Cellular Physiology, 1995, 164(1):17-25 reports that retinoic acid increases the expression of metalloproteases in rat osteoblasts while simultaneously the mRNA levels of TMP-1 were clearly reduced depending on the dose of retinoic acid administrated. The work of Heath et al., Biochemical and Biophysical Research Communications 1990, 168(3): 1171-1176 describes that the TIMP levels decreased to 0 under the influence of retinol.

Considering the above-described state of the art it is a surprising result for those skilled in the art that by the effect of vitamin A, i.e. retinoic acid and retinol, not only a clear inhibition of the expression of MMP-9 metalloprotease in alveolar macrophages and blood monocytes but simultaneously also a stimulation of the TIMP-1 inhibitor is achieved.

In the frame of experiments to determine the uptake of liposomes according to the invention by monocytes in blood there were used as test systems also various conventional cell lines of different origin and examined with respect to their capability to take up liposomes. Particularly, cells of myelomonocytic origin were used such as the cell lines HL-60, U937, THP-1, and Mono Mac 6 (mentioned in the order of increasing degree of maturity). Thus, the monocytic human cell line Mono Mac 6 has reached the highest degree of maturity on its way to develop into a macrophage. However, this cell has taken up almost no liposomes which is in contrast to the assumption that a cell with a higher degree of differentiation also shows a higher phosphatidylserine receptor expression. Insofar it was also not obvious that alveolar macrophages would take up these liposomes in a selective manner. Furthermore, it was unpredictable into which type of macrophage a blood monocyte would develop since there are significant differences not only with respect to morphology and function. Moreover, it was unknown which cells are endowed with what kind of phosphatidylserine receptor. Particularly, it was unknown that a phosphatidylserine receptor is present on alveolar macrophages. For this reason, not only the effect of vitamin A in the treatment of COPD and lung emphysema was surprising but also the increased efficacy of vitamin A due to its administration in the form of liposomes, particularly by specifically composed liposomes as presently described.

By treatment of COPD and lung emphysema with vitamin A the imbalance between MMPs and TIMPs may be treated, i.e. the expression of the former is inhibited while the expression of the latter is stimulated.

The therapy described herein counteracts tissue destruction and provides a novel and promising approach for the treatment of chronic obstructive lung disorders. Among others, the particular advantages of the invention are:

- use of a smaller dose due to selective uptake of liposomally packaged vitamin A by the alveolar macrophages which are the most important source of metalloproteases;
- a highly efficient effect of vitamin A is achieved by the simultaneous impact on two agonists in equilibrium of the proteolytic system of the lung;
- the protease/antiprotease equilibrium in the lung is returned to normal;
- liposomally packaged vitamin A is stored in the form of a depot;
- this results in a lower amount of vitamin A released into the blood circulation, the active agent remains directly at the site of activity, i.e. the lung, and the systemic side effects are decreased.

The following experiments demonstrate the surprising effects of vitamin A administration, particularly in the form of liposomes. For this purpose, human alveolar macrophages (AMs) were obtained via bronchial lavage. The AMs were seeded into Mono Mac 6 medium+10% FCS onto a 24 well "low attachment" plate (Costar) using $1 \times 10^6$ cells in a volume of 1 ml per each sample. Additions of vitamin A liposomes or of the pure substances, respectively, were carried out. Cells for RT-PCR or culture supernatant for protein determinations by means of ELISA, respectively, were harvested from parallel samples each on day 1, day 3, and day 4. Specifically, the following samples were prepared:

β=control sample, AMs in medium only

Lipleer=empty liposomes

LipVitA=liposomes containing vitamin A (retinoic acid, Sigma R-2625) 5 µM final

VitA=pure vitamin A (retinoic acid, Sigma R-2625) 5 µM final

LipPalm=liposomes containing all-trans retinol palmitate (Sigma R-3375) 3 µM final Palmitat=all-trans retinol palmitate (Sigma R-3375) 3 µM final The culture supernatants were monitored for MMP-9 and TMP-1 content using commercial ELISA kits (Amersham Pharmacia). In each case the numerals refer to ng/ml culture supernatant based on $1 \times 10^6$ cells.

Figure 1:
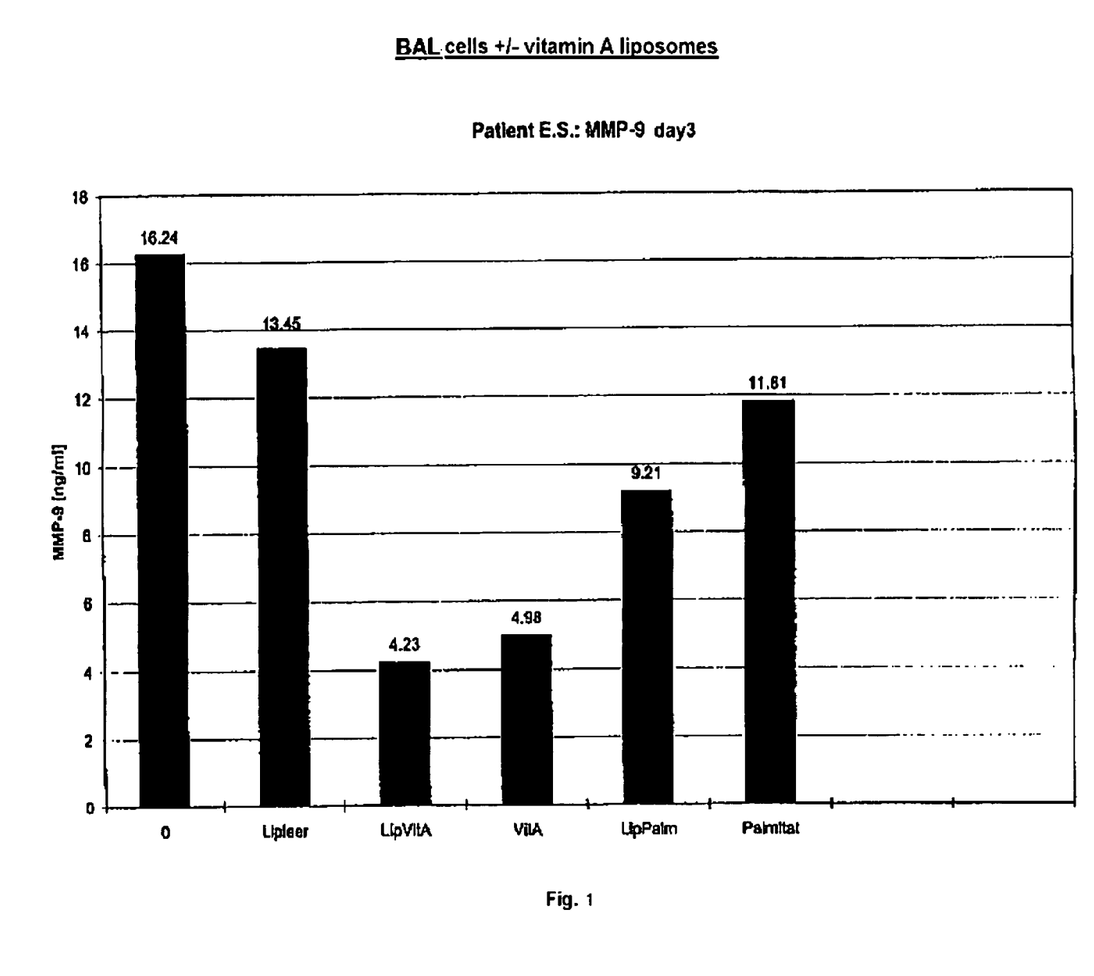
FIG. 1: BAL cells +/− vitamin A liposomes—patient E.S.: MMP-9 day 3.
Figure 2:
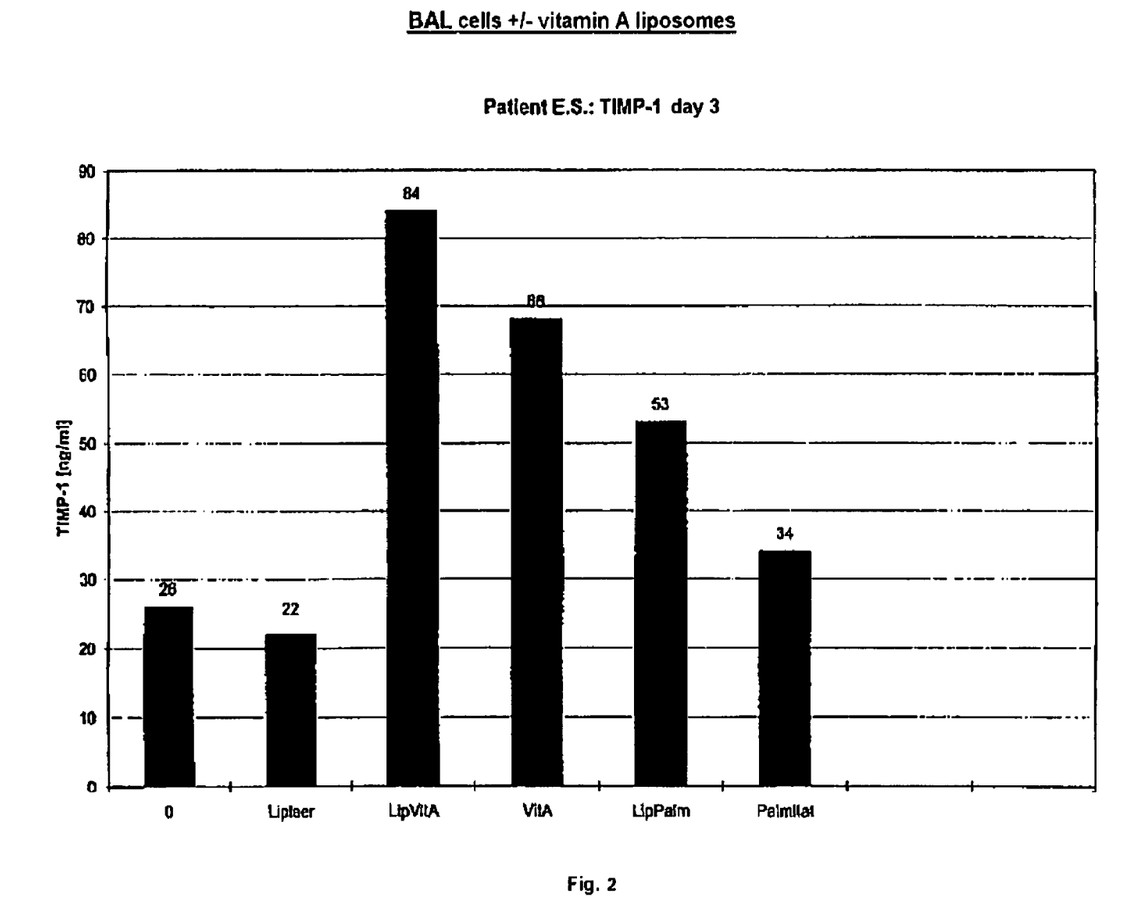
FIG. 2: BAL cells +/−vitamin A liposomes—patient E.S.: TIMP-1 day 3.
Figure 3:
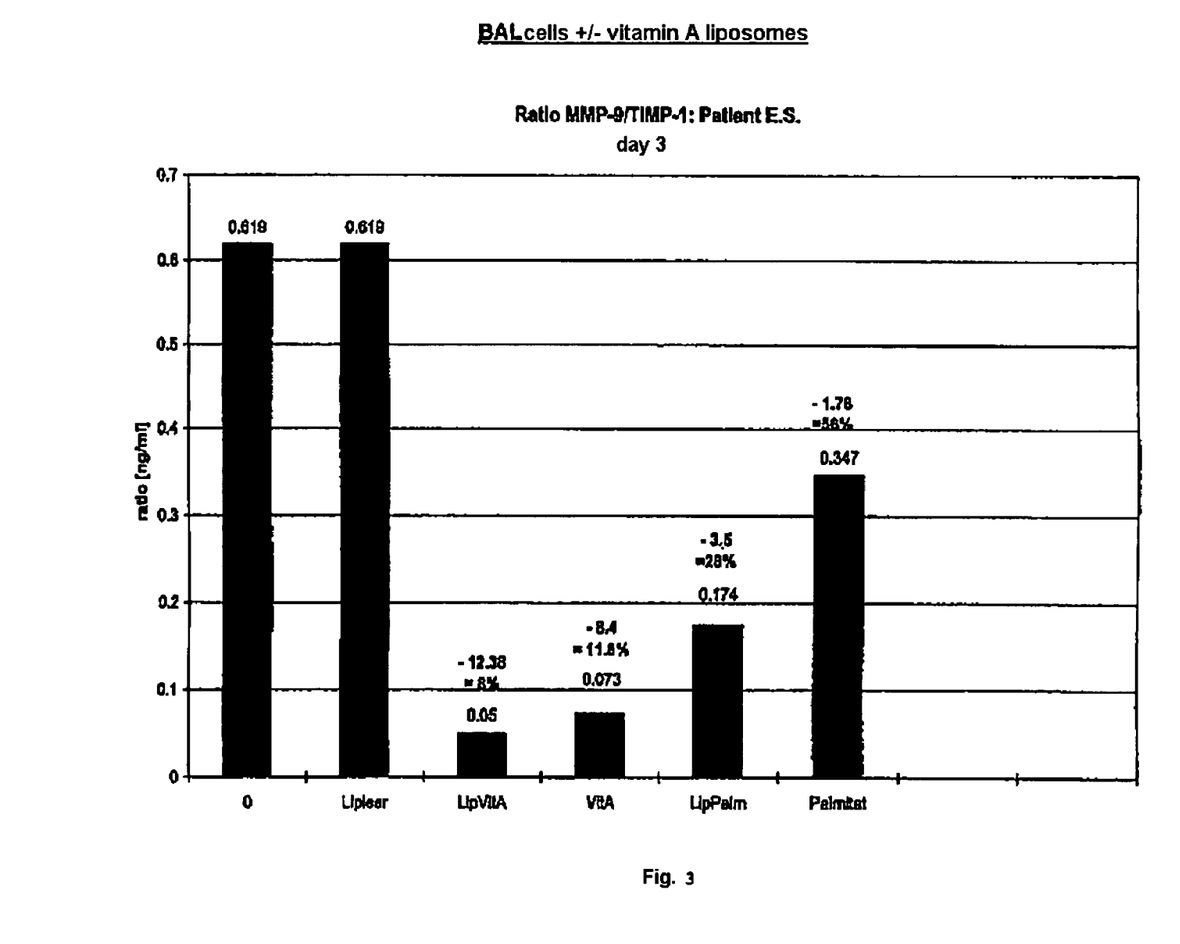
FIG. 3: BAL cells +/− vitamin A liposomes—ratio MMP-9/TIMP-1: patient E.S. day 3.
Figure 4:
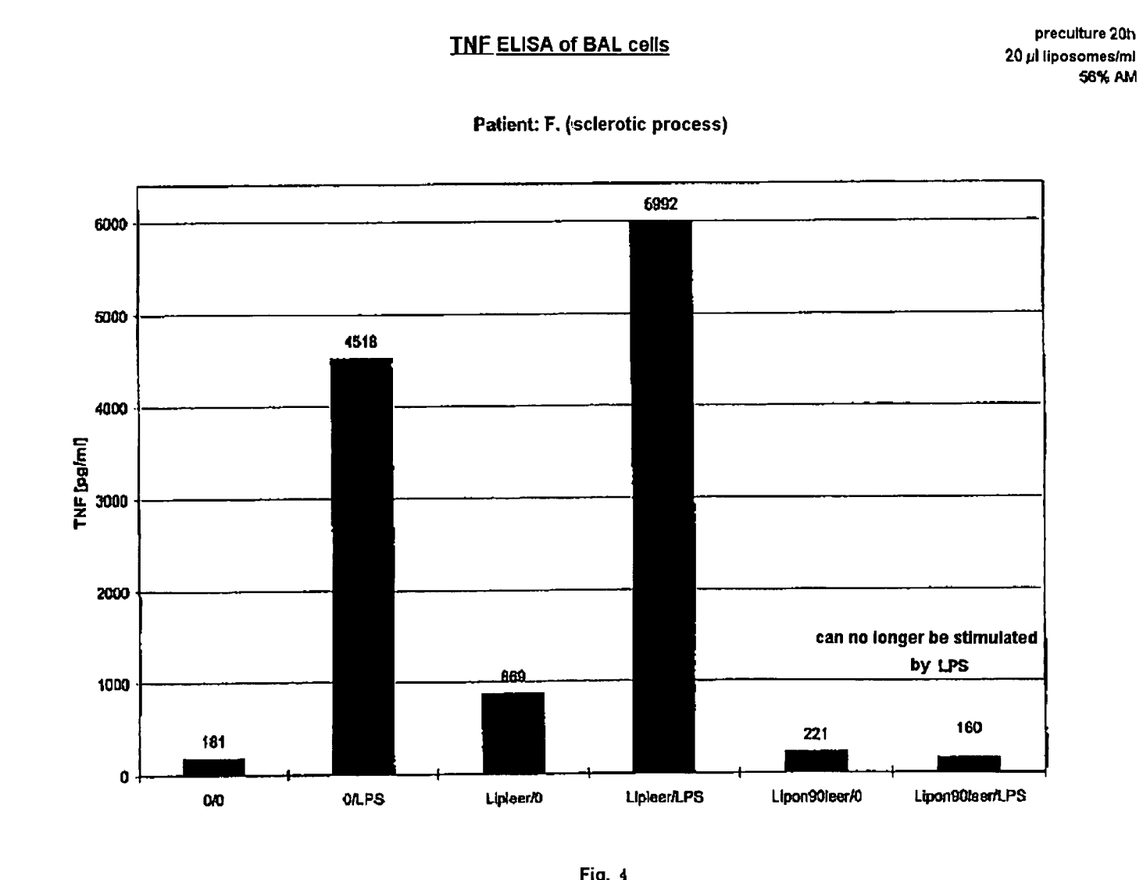
FIG. 4: TNF ELISA of BAL cells patient: F. (sclerotic process)
Figure 5:
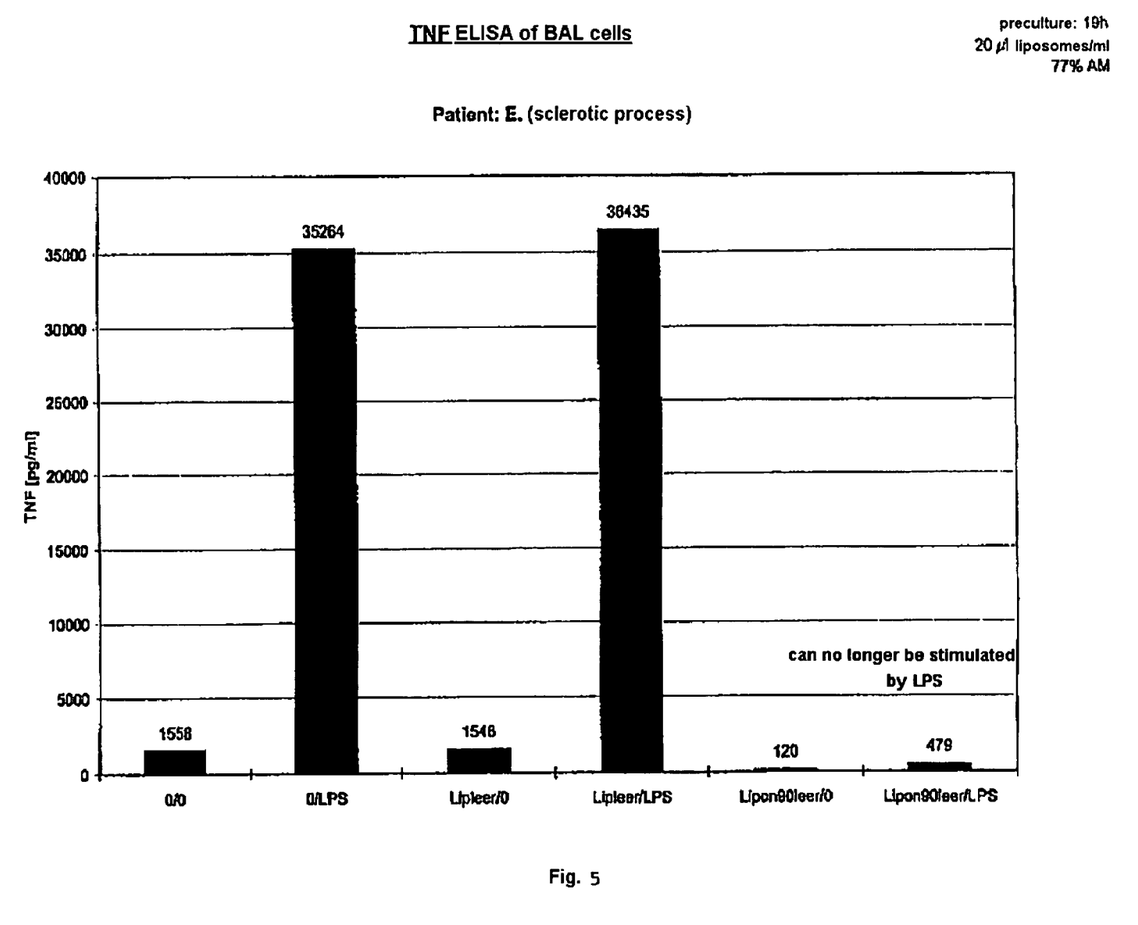
FIG. 5: TNF ELISA of BAL cells patient: E. (sclerotic process)
Figure 6:
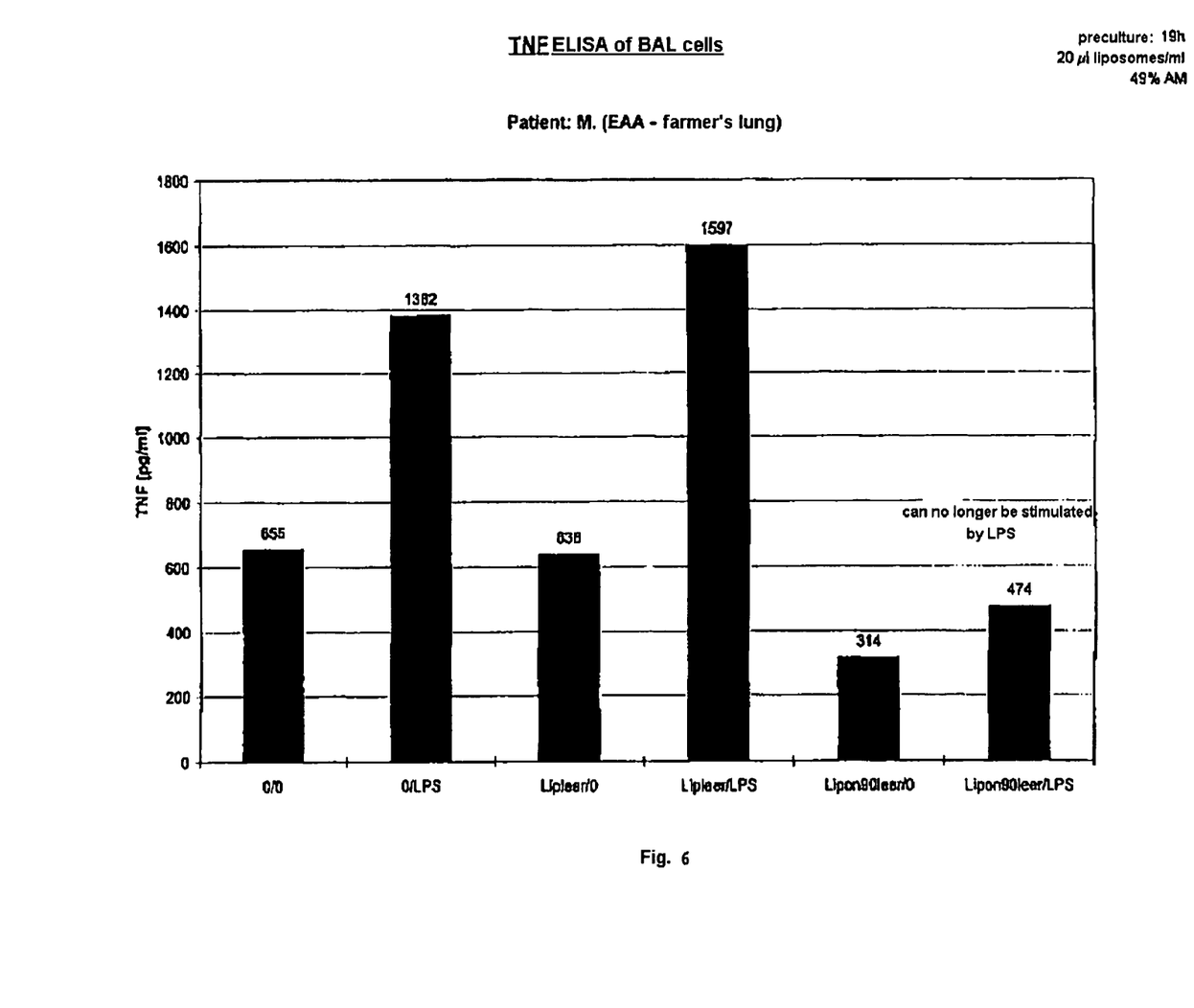
FIG. 6: TNF ELISA of BAL cells patient: M. (EAA—farmer's lung)
Figure 7:
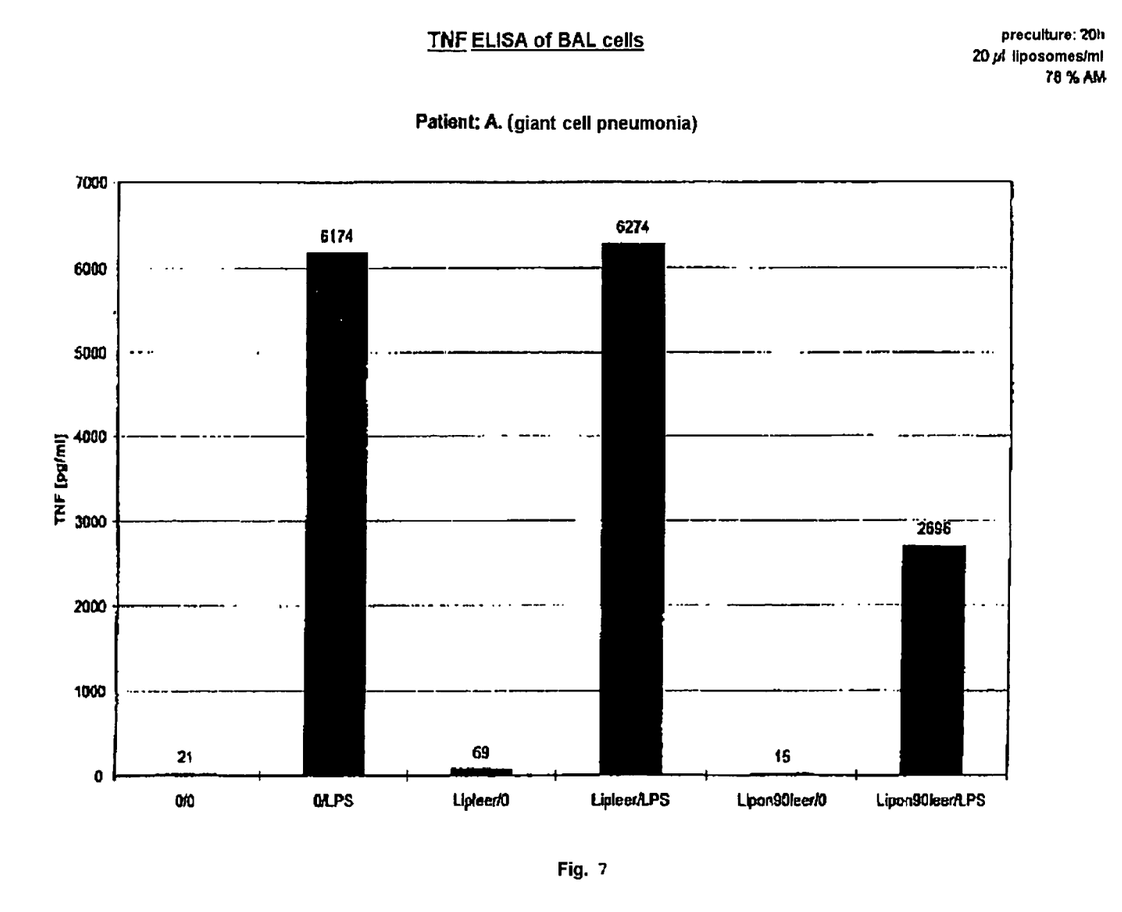
FIG. 7: TNF ELISA of BAL cells patient: A. (giant cell pneumonia)

The data given show the results obtained on day 3 following vitamin A addition. On day 1, no effect could be observed on the protein level (but on the RNA level); the data obtained on day 4 were the same as those of day 3: while due to liposomal and free vitamin A the MMP-9 expression is strongly reduced a simultaneous increase in TIMP-1 is observed. In each case the effect of liposomal vitamin A is superior to that of free vitamin A. This opposite regulation of MMP-9 and TIMP-1 also explains the drastic effect on the MMP-9/TIMP-1 ratio of the vitamin A treatment.

The culture of BAL cells and PBMCs with liposomal vitamin A is performed as follows:

Material:

RPMI 1640 (Biochrom # F1415, Berlin), L-glutamine 2 mM (Gibco # 25030-024), penicillin 200 U/ml, streptomycin 200 µg/ml (Gibco # 15140-114), non-essential amino acids (NEAA) 1-2x (Gibco # 11140-35), OPI supplement (contains oxalacetate, Na pyruvate and insulin) 10 ml per 1 liter (Sigma # O-5003). Following filtration through a Gabro ultrafilter U 2000 (Martinsried, Germany) to remove LPS addition of 10% FCS, LPS tested.

Costar low attachment 24 well plates # 3473 (Bodenheim, Germany) $1 \times 10^6$ BAL cells (=cells obtained by brochoalveolar lavage containing alveolar macrophages in an amount of about 80%) or $1.5 \times 10^6$ PBMCs (=peripheral blood mononuclear cells isolated via LymphoPrep gradient (Nycomed, Norway)), respectively, in a volume of 1 ml were used per sample. Pretreat the 24 well low attachment cell culture plate according to the manufacturer's instructions. For this purpose, fill the respective wells with 1 ml of medium and incubate for 20 min at 37° C. in an incubator. Afterwards remove the medium and replace by cell suspension. Add the liposomes loaded with vitamin A in a final concentration of $5 \times 10^{-6}$ M. Prepare parallel samples with pure vitamin A and empty liposomes as controls. For the measurement of MMP-9 and TIMP-1 in the culture supernatant and for determination of mRNA expression incubate the cells in an incubator for three days at 37° C. Afterwards resuspend the cells carefully and first remove 2×10⁴ cells per PCR lysate for lysis in 200 µl of RNAclean (AGS, Heidelberg, Germany)in an Eppendorf reaction vial. Store these PCR lysates at −20° C. until further use. Transfer the remaining cell suspension into an Eppendorf vial and centrifuge for 5 min at 14,000×g. Remove the supernatant, transfer into a fresh vial and store at −80° C. until measurement.

Summary of the Samples:
1. BAL cells or PBMCs, respectively without any addition
2. BAL cells or PBMCs, respectively + empty liposomes
3. BAL cells or PBMCs, respectively + liposomes vitA 5 µM final
4. BAL cells or PBMCs, respectively pure vitA 5 µM final Determinations of MMP-9 and TIMP-1 on the Protein Level by ELISA For the measurement of MMP-9 and TIMP-1 in cell culture supernatants commercially available ELISA kits of Amersham Pharmacia Biotech company (Freiburg, Germany) are used. Specifically, the kits are:

Matrix metalloproteinase-9 (MMP-9), human, ELISA system: code RPN 2614
Tissue inhibitor of metalloproteinases-1 (TIMP-1), human, ELISA system: code RPN 2611
Matrix metalloproteinase-9 (MMP-9), human, activity system: code RPN 2630

The ELISAs were always performed exactly according to the manufacturer's instructions.

Determinations of mRNA Expression of MMP-9 and TIMP-1 by Means of Semi-quantitative RT-PCR The method used is established and already published in several publications. Therefore, only some points are listed for description.
isolation of total RNA using the RNAclean method
transcription of the RNA into cDNA using oligo-dT
amplification of the cDNA using specific primers for MMP-9, TIMP-1, and α-enolase as a control
confirmation by agarose gel Preparation of Liposomes Containing 5×10⁻⁴ M of All-trans Retinoic Acid Reagents:
phosphatidyl choline: 1-palmitoyl-2-oleyl-sn-glycero-3-phosphocholin=POPC
phosphatidyl serine: 1,1-dioleyl-sn-glycero-3-phospho-L-serine, mono sodium salt=OOPS
all-trans retinoic acid (vitamin A): Sigma # R-2625 (Deisenhofen, Germany) 10 mM stock solution in absolute ethanol
(±)-α-tocopherol (vitamin E): Sigma # T-3251 (Deisenhofen) stock solution 20 mg/ml in absolute ethanol Be careful to ensure that all reagents used are endotoxin-free (LPS-free) and render all glass ware LPS-free by baking at 180° C. for 3 h. Charge 17.5 mg POPC and 7.5 mg OOPS into a sterile freezing tube (NUNC) to prepare 1 ml liposomes. Dissolve lipids by addition of 1 ml chloroform (Merck). Transfer the complete solution into a 250 ml Duran glass round bottom flask and add 50 µl of the vitamin A stock solution with a pipette. Additionally add 10 µl of the vitamin E stock solution to protect lipids and vitamin A from oxidation. Under sterile conditions, evaporate the chloroform during gentle heating (not more than 42° C.) and rotation of the flask until a whitish lipid film forms at the inner glass surface. Reconstitute the liposomes by addition of 1 ml sterile LPS-free phosphate buffer (PBS) and agitation of the flask. For complete reconstitution of the liposomes let the preparation rest for about 20 min at room temperature (protected from light). Afterwards, transfer the resulting multilamellar liposomes into a sterile 1.5 ml Eppendorf reaction vial. For control purposes, always prepare 'empty' liposomes without vitamin A addition. To remove vitamin A not encapsulated into liposomes centrifuge the liposome preparation in an Eppendorf table top centrifuge at 14,000×g for 5 min. Pipette off the supernatant and restore the volume to 1 ml using fresh PBS. Repeat this washing step for a total of 6 times.

In the subsequent extrusion process the multilamellar liposomes are converted into unilamellar liposomes having a diameter of 0.4 µm. For this purpose, the extruder is assembled according to the instructions of the manufacturer (Lipex Biomembranes, Vancouver, Canada). To obtain 0.4 µm liposomes a filter with a pore size of 0.4 µm (Costar Nuclepore # 110 407) is inserted in addition to the preliminary filter (Drain Disc, Costar # 230 300). Charge the complete volume of liposomes into the top of the device using a Pasteur pipette. Extrude liposomes under pressure (about 5-10 bar, not more than 40 bar) and recover in an Eppendorf reaction vial. Recharge these liposomes into the top of the device and repeat (the membrane filter may be used up to 9 times). A liposome preparation should be subjected to this cycle at least three times (preferably five times). For use in cell culture, subject the finished unilamellar liposomes a sterile filtration through Millipore # SLGV 013 OS filter in a sterile work bench. A liposome preparation prepared in this way may be used for at least four weeks.

Characterization of the Liposomes
unilamellar
0.4 µm in diameter
confirmation of functionality may be carried out using a specific staining method and analysis via flow cytometer (may be described in detail if necessary)

What is claimed is:

1. A method for treating a tracheo-bronchial tract disease in a subject in need thereof, the method comprising:
   (a) selecting a subject with a tracheo-bronchial tract disease selected from the group consisting of chronic obstructive pulmonary disease (COPD), chronic bronchitis, and emphysema; and
   (b) administering to the subject a pharmaceutical composition in the form of an aerosol inhalant comprising a therapeutically effective amount of vitamin A, a vitamin A derivative, or a combination thereof encapsulated within a unilamellar liposome, wherein:
      (i) the vitamin A derivative is selected from the group consisting of retinol, retinal, retinoic acid, β-carotene, and esters thereof;
      (ii) the lipid composition in the lipid bilayer of said unilamellar liposome consists of phosphatidylcholine and at least one other phospholipid selected from the group consisting of phosphatidylinositol, phosphatidylserine, and a cardiolipin;
      (iii) the unilamellar liposome targets the therapeutically effective amount of the vitamin A, the vitamin A derivative, or the combination thereof to alveolar macrophages; and
      (iv) the unilamellar liposome has a diameter of about 0.1 µm to about 0.4 µm.

2. The method of claim 1, wherein the tracheo-bronchial tract disease is chronic obstructive pulmonary disease (COPD).

3. The method of claim 1, wherein said liposomes contain 0.0015 mg to 5.0 mg of the vitamin A, vitamin A derivative, or the combination thereof per 25 mg lipids.

4. The method of claim 3, wherein said liposomes contain 0.05 mg to 0.30 mg of the vitamin A, vitamin A derivative, or the combination thereof per 25 mg lipids.

5. The method of claim 1, wherein said esters thereof are selected from the group consisting of saturated and unsaturated fatty acid esters of retinol and saturated and unsaturated fatty acid alcohol esters of retinoic acid.

6. A method for treating a tracheo-bronchial tract disease in a subject in need thereof, the method comprising:
 (a) selecting a subject with a tracheo-bronchial tract disease selected from the group consisting of chronic obstructive pulmonary disease (COPD), chronic bronchitis, and emphysema; and
 (b) administering to the subject a pharmaceutical composition in the form of an aerosol inhalant comprising a therapeutically effective amount of vitamin A, a vitamin A derivative, or a combination thereof within a unilamellar liposome, wherein:
  (i) the vitamin A derivative is selected from the group consisting of retinol, retinal, retinoic acid, β-carotene, and esters thereof;
  (ii) the lipid composition in the lipid bilayer of said unilamellar liposome consists of phosphatidylcholine and at least one other phospholipid selected from the group consisting of phosphatidylinositol, phosphatidylserine, and a cardiolipin, and further wherein a ratio of said phosphatidylcholine to said at least one other phospholipid is 75:25 to 65:35; and
  (iii) the unilamellar liposome targets the therapeutically effective amount of the vitamin A, the vitamin A derivative, or the combination thereof to alveolar macrophages; and
  (iv) the unilamellar liposome has a diameter of about 0.1 μm to about 0.4 μm.

7. A method for treating a tracheo-bronchial tract disease in a subject in need thereof, the method comprising:
 (a) selecting a subject with a tracheo-bronchial tract disease selected from the group consisting of chronic obstructive pulmonary disease (COPD), chronic bronchitis, and emphysema;
 (b) administering to the subject a pharmaceutical composition in the form of an aerosol inhalant comprising a therapeutically effective amount of vitamin A, a vitamin A derivative, or a combination thereof within a unilamellar liposome, wherein:
  (i) the vitamin A derivative is selected from the group consisting of retinol, retinal, retinoic acid, β-carotene, and esters thereof;
  (ii) the lipid composition in the lipid bilayer of said unilamellar liposome consists of phosphatidylcholine and at least one other phospholipid selected from the group consisting of phosphatidylinositol, phosphatidylserine, and a cardiolipin;
  (iii) the unilamellar liposome targets the therapeutically effective amount of the vitamin A, the vitamin A derivative, or the combination thereof to alveolar macrophages;
  (iv) the unilamellar liposome has a diameter of about 0.1 μm to about 0.4 μm; and
  (v) the unilamellar liposome reduces a ratio of expression of matrix metalloprotein-9 (MMP-9) to expression of tissue inhibitor of metalloprotease-1 (TIMP-1) in said alveolar macrophages.

8. The method of claim 7, wherein a ratio of said phosphatidycholine to said at least one other phospholipid in said unilamellar liposome is 75:25 to 65:35.

* * * * *

UNITED STATES PATENT AND TRADEMARK OFFICE
CERTIFICATE OF CORRECTION

PATENT NO. : 7,476,380 B2 Page 1 of 1
APPLICATION NO. : 11/127986
DATED : January 13, 2009
INVENTOR(S) : Frankenberger et al.

It is certified that error appears in the above-identified patent and that said Letters Patent is hereby corrected as shown below:

On title page, item (73) Assignee:

replace "GSE"

with --GSF--.

Signed and Sealed this

Seventeenth Day of March, 2009

JOHN DOLL
*Acting Director of the United States Patent and Trademark Office*